United States Patent
Schrott et al.

(10) Patent No.: US 10,300,088 B2
(45) Date of Patent: May 28, 2019

(54) METHOD FOR PRODUCING EYE DROPS

(71) Applicant: HERR MARC SCHROTT, CENTRAL APOTHEKE, Steinbach/Ts (DE)

(72) Inventors: Marc Schrott, Eppstein (DE); Andrea Jochheim-Richter, Königstein (DE)

(73) Assignee: Herr Marc Schrott, Central Apotheke (DE)

( * ) Notice: Subject to any disclaimer, the term of this patent is extended or adjusted under 35 U.S.C. 154(b) by 0 days.

(21) Appl. No.: 15/559,653

(22) PCT Filed: Mar. 22, 2016

(86) PCT No.: PCT/EP2016/056197
§ 371 (c)(1),
(2) Date: Sep. 19, 2017

(87) PCT Pub. No.: WO2016/150932
PCT Pub. Date: Sep. 29, 2016

(65) Prior Publication Data
US 2018/0050064 A1 Feb. 22, 2018

(30) Foreign Application Priority Data
Mar. 24, 2015 (DE) .................. 10 2015 205 293

(51) Int. Cl.
*A61K 35/16* (2015.01)
*A61M 1/02* (2006.01)
*A61K 9/00* (2006.01)
*A61J 1/05* (2006.01)
*A61K 9/08* (2006.01)
*A61K 47/69* (2017.01)
*A61K 33/20* (2006.01)
*A61K 47/46* (2006.01)

(52) U.S. Cl.
CPC .................. *A61K 35/16* (2013.01); *A61J 1/05* (2013.01); *A61K 9/0048* (2013.01); *A61K 9/08* (2013.01); *A61K 33/20* (2013.01); *A61K 47/6957* (2017.08); *A61M 1/0272* (2013.01); *A61K 47/46* (2013.01)

(58) Field of Classification Search
CPC ................................. A61K 35/14; A61K 35/16
See application file for complete search history.

(56) References Cited

U.S. PATENT DOCUMENTS

| 6,043,213 A | 3/2000 | Tsubota | |
| 2003/0032930 A1* | 2/2003 | Branch | B65D 35/28 604/298 |
| 2008/0299212 A1 | 12/2008 | Kim et al. | |
| 2012/0171658 A1 | 7/2012 | Bein et al. | |
| 2015/0064133 A1 | 3/2015 | Woods et al. | |

FOREIGN PATENT DOCUMENTS

| DE | 10 2009 022 793 A1 | 12/2010 |
| DE | 20 2011 004 487 U1 | 6/2012 |
| EP | 1 380 351 A1 | 1/2004 |
| WO | 2010/136535 A1 | 12/2010 |
| WO | 2014/108852 A1 | 7/2014 |

OTHER PUBLICATIONS

Murador et al, Autologous serum eye drops in treatment of dry-eye syndrome: Experience of botucatu blood center and department of ophthalmology of botucatu medical school, Sao Paulo, Brazil. Transfusion, (Sep. 2009) vol. 49, Supp. Suppl. 3, pp. 157A-158A. (Year: 2009).*
International Search Report for International Application No. PCT/EP2016/056197 dated May 27, 2016.
Geerling,G. et al., Autologous Serum Eye Drops for Ocular Surface Disorders, British Journal of Ophthamology, vol. 88, No. 11, Nov. 2004, pp. 1467-1474.
Reed-Kane D., et al., Applications and Sterility of Autologous Serum Eye Drops, International Journal of Pharmaceutical Compounding 2009, vol. 13, No. 6, Nov./Dec. 2009, pp. 540-543.
Europaisches Arzneibuch,Grundwerk 2005, pp. 865-867.
Gesetz uber den Verkehr mit Arzneimitteln (Arzneimittelgesetz—AMG) Dec. 2005.
Gesetz zur Regelung des Transfusionswesens (Transfusionsgesetz—TFG) Aug. 2007.
Therapie der Keratokonjunktivitis sicca mit Augentropfen aus autologem Serum, Dec. 2012.
Vergleich der epitheliotrophen Kapazitat von Serum und Plasma, am Modell einer immortalisierten humanen Hornhautepithelzelllinie, 2008.

* cited by examiner

*Primary Examiner* — Qiuwen Mi
(74) *Attorney, Agent, or Firm* — Seth L. Hudson; Clements Bernard Walker, PLLC

(57) ABSTRACT

The invention relates to a method for producing eye drops, the thus obtained eye drops and to a kit which comprises the eye drops.

8 Claims, No Drawings

METHOD FOR PRODUCING EYE DROPS

FIELD OF THE INVENTION

The present invention relates to a method for producing eye drops, to the eye drops thus obtained, and to a kit comprising the eye drops.

BACKGROUND OF THE INVENTION

Dry eye syndrome is one of the most frequent diseases in the field of ophthalmology, the prevalence increasing with age. According to the definition by the "Dry Eye Workshop Study Group" (DEWS Steering Committee), the dry eye syndrome is a multifactorial disturbance of the tear film and eye surface, which is accompanied by physical-psychic discomfort or visual impairment. Inflammatory processes and a hyperosmolar tear film are important factors associated with this clinical picture.

The clinical picture of the dry eye is often understood to be keratoconjunctivitis sicca. "Keratoconjunctivitis sicca" refers to a disease of the eye surface accompanied by typical symptoms, such as a foreign body sensation, light sensitivity, itching, burning pain, and a feeling of pressure. In addition, visual reduction, reddened eyes, epiphora (constant tearing) and a dry eye sensation are often observed. When the tear production is reduced, the complaints occur preferentially in the morning. If the problem resides in an increased evaporation of the lacrimal fluid, the symptoms occur more frequently in the evening.

Today, a wide variety of artificial tear substitutes in the form of eye drops, eye gel or eye spray are offered for treating dry eye syndrome. For example, there may be mentioned the replacement or supplementing of the aqueous phase of the lacrimal fluid by aqueous solutions of thickening agents, such as povidone, hyproxymellose or carboxymethylcellulose, salts and optionally further active substances, such as hyaluronic acid or lipids. Also known is the supplementing of the surface lipid layer of the tear film by a liposomal eye spray, which reduces the evaporation of the natural lacrimal fluid and avoids premature draining as a tear beyond the lash line. Further known is the replacement of the tear film and the reduction of the shear forces between the eye surface and lid during the lid movements by fat-containing ointments. In particular, such ointments are oil-in-water emulsions.

A disadvantage of these known products is the fact that they have a relatively short dwelling time on the cornea. This is the reason why the corresponding treating agent must be applied on a regular basis, which is often unpleasant for the patient, or even impossible in some situations. For example, in a distinctly dry eye, one drop each of an aqueous phase should be dripped into either eye every 30 to 60 minutes, in order to compensate for existing deficits. With treating agents in gel form, this drawback is avoided at least in part. However, it is found difficult here to supply the cornea sufficiently with oxygen. In addition, just like with ointments, the vision may be impaired for some seconds or even minutes. If the corresponding agents include preservatives, these may lead to allergic responses on the one hand. In addition, when permanently and frequently applied, this may lead to a deterioration of the dry eye symptoms.

Further, the use of punctal plugs is known. When the lacrimal fluid produced by the lacrimal gland is drained to the nose, the lacrimal fluid is initially distributed by blinks over the cornea in order to keep it wet. Subsequently, it is drained from the conjunctival sac through the lacrimal puncta (puncta lacrimalia). Punctal plugs are inserted into one or both lacrimal puncta to reduce this drain. Depending on their nature, the plugs may permanently remain in the lacrimal puncta, or dissolve after a few weeks. The essential disadvantage of this method is the fact that the retaining of the lacrimal fluid at the same time also causes the inflammation-promoting substances in the lacrimal fluid, which has an altered composition in dry eyes, to remain longer on the eye. In addition, the draining of lacrimal fluid through the effluent tear ducts, which is reduced by the plugs, may promote infections by bacteria that may ascend from the nasal cavity.

Especially in pronounced diseases of the eye surface, it was found that the known artificial tear substitutes or the use of punctal plugs not necessarily leads to the desired success. The artificial tear substitutes always contain only some components of natural tears. A sustainable therapy is hardly possible in such a case.

A relatively new approach in the therapy of diseases of the eye surface includes the use of eye drops made from serum, especially the patient's own serum. An advantage thereof is the fact that corresponding eye drops have some biomechanical and biochemical similarity with the lacrimal fluid. The therapeutic success here is better than that obtained with otherwise usually employed artificial tear substitutes, as shown by E. M. Herold ("Therapie der Keratokonjunktivitis Sicca mit Augentropfen aus autologem Serum", Inaugural Dissertation of Erlangen Nürnberg University, Dec. 20, 2012). The patient's own serum means autologous serum obtained from the blood of the person who later employs the eye drops prepared therefrom.

BRIEF SUMMARY OF THE INVENTION

A possible method for preparing eye drops from the patient's own serum has been described by Herold (loc. cit.), for example. In this method, 100 ml of blood is collected from the patient. The blood count is checked before and after the collection. After centrifugation, the supernatant is filtered off under sterile conditions and filled into sterile dropper bottles. Immediately thereafter, the dropper bottles are frozen at not higher than −18° C. Thawed bottles should be stored at +2° C. to +6° C. for one week at most.

The high proportion of proteins in the serum causes microbial vulnerability. However, the use of stabilizers or preservatives as well as pasteurization is not possible, or not desirable. The omission of preservatives or antibiotics in corresponding eye drops prepared with the patient's own serum causes the potential risk of bacterial contamination, which exists, in particular, when the eye drops are used for a longer period of time from the same dosing vessel or administration container. In addition, the treatment of keratoconjunctivitis sicca is usually scheduled to a period of 6 months or longer. However, a collected volume of 100 ml of the patient's own blood as known from the prior art is not sufficient to perform the treatment over an extended period of time. In addition, since the blood collection is usually felt as unpleasant by the person concerned, there is a need for a production method that contributes to a higher compliance and thus to the success of the corresponding treatment. In addition, the other disadvantages from the prior art should also be avoided if possible.

Surprisingly, it has been found that the object of the present invention is achieved by a process for producing ready-to-use eye drops, especially for the treatment of dry eye syndrome, comprising the following steps:
 a) collecting whole blood in a first place, followed by
 b) separating the blood to obtain serum,
 c) examining the serum for the presence of pathogens, followed by
 d) filling the serum into at least one administration means in a second place,
 wherein said first and second places are different.

Preferably, the process further comprises step e) final examinations for sterility before the eye drops are released as a medicament.

Optionally, the identity and/or purity may also be checked additionally in the final examination.

DETAILED DESCRIPTION OF THE INVENTION

Ready-to-use eye drops within the meaning of the present invention are eye drops that can be immediately employed by persons. The delivery of serum eye drops is a pharmacy-only process. In the process according to the invention, the filling of the serum into an administration means is effected in a pharmacy. The blood collection itself is performed in a different place. This is not possible, for example, with a device as described in WO 2010/136535 A1, since the blood collection bag is directly connected with the administration means. Performing the blood collection in one place, for example, at the blood donation service, and the filling of the serum in a second place, namely according to the legal regulation in a pharmacy, enable the eye drops to be delivered in a pharmacy, for example, near the place of residence or near the working place of the user.

The collection of blood quantities larger than 100 ml or more than 200 ml, for example, 500 ml, is preferably effected within the scope of a whole blood donation. "Blood" or "whole blood" means the blood that contains all the native components. According to the standard procedure, the whole blood donation can be performed by a transfusion physician, for example, in corresponding blood donation centers. A whole blood donation in which about 500 ml of blood are collected enables about 230 ml of serum to be obtained after the separation of the blood. From this serum, eye drops can be obtained that enable one person suffering from dry eye syndrome to be supplied over a period of up to half a year. Thus, the process according to the invention enables a long-term treatment without requiring a further blood collection, which results in an improved compliance and thus also in a better treatment success.

The collection of 500 ml of blood corresponds to the amount of blood usually collected within the scope of a whole blood donation. The collection of more than 500 ml of blood and the further processing into eye drops from the patient's own serum is possible in principle. However, from a medical point of view, it is recommended to limit a blood donation to an amount of 500 ml. Collecting such an amount is not harmful to the human organism. According to the invention, it is also possible to collect less than 500 ml of blood, such as 300 ml, 350 ml, 400 ml, or 450 ml. With such amounts, a long-term supply of persons with serum eye drops is still possible. However, the collection of less than 200 ml of blood is not to be recommended, because a more frequent blood collection will then be necessary, which reduces the compliance and thus the success of treatment.

According to the invention, the whole blood may be autologous or allogenic whole blood. "Autologous whole blood" means that the eye drops obtained from the serum are exclusively employed by the person who has also donated the blood. In the case of allogenic whole blood, the blood donator and the user of the eye drops are different persons.

The use of autologous whole blood has the advantage that only endogenous substances are present in the eye drops obtained from the patient's own serum. For example, if persons are not capable of donating blood themselves, for example, because of physical limitations, an allogenic blood donation still enables these persons to be supplied with serum eye drops. Thus, allogenic whole blood enables a treatment that would not be possible with autologous whole blood here, because the latter is not available.

Because of the many possibilities to check the whole blood and the serum in the process according to the invention, the compliance for serum eye drops from allogenic whole blood can be improved, and the safety of the product in terms of the absence of contaminants can be increased.

The separation of the blood into its components is effected by coagulation. This is preferably done over a period of from 15 minutes to 70 minutes at room temperature. "Room temperature" within the meaning of the present invention is a temperature within a range of from 15° C. to 30° C., especially from 18° C. to 25° C. "Coagulation" means the clotting of blood. This causes the blood components to separate. After the coagulation, it is possible according to the invention to store the blood at +2° C. to +8° C. The storage can be effected over night, for example, but should not exceed a period of 48 hours because of the microbial vulnerability of the serum. In addition, an enzymatic decomposition of the blood components starts after about 48 hours. On the other hand, a storage for 12 to 48 hours is preferred because it can ensure that the coagulation is complete.

After the coagulation, a centrifugation of the blood that has already been separated at least in part by the coagulation is preferably effected, optionally after intermediate storage. The centrifugation is preferably performed over a period of from 5 to 20 minutes, especially from 5 to 15 minutes, at 1000 to 3500 revolutions/min, especially at 1000 to 3000 revolutions/min. Then, the transfer of the thus obtained cell-free serum from the original blood collection device, for example, a blood bag, into a container suitable for serum is effected at room temperature. This container is preferably an empty blood bag (empty bag, serum bag), which can be sealed through a connection hose with the blood bag containing the separated blood. A contamination of the serum by outer influences can be almost avoided thereby.

Thus, a serum is obtained by the separation of the blood, which is preferably effected by means of coagulation and centrifugation. The physiological serum osmolarity (isotonicity) is usually from 281 to 297 mosmol/l in humans. This value corresponds to that of lacrimal fluid, which results in the preferred use of eye drops from the patient's own serum in the treatment of eye diseases and, in particular, of dry eye syndrome. Further, the pH values of both serum and human tears is about 7.4.

Before being filled into suitable administration means, the serum obtained is examined for the presence of pathogens. Pathogens within the meaning of the present invention include any kind of infectious pathogens or other factors causing or promoting diseases that may have adverse effects on the human organism and, especially when eye drops are used, could jeopardize the success of the therapy, or could possibly lead to the formation of further diseases. Contaminations of the serum may also have happened, for example, during the blood collection or the separation of the blood. In particular, the incorporation of germs is possible after inappropriate skin disinfection, and/or when there are leaks in the blood bag flexible tube system.

In addition to the examination of the serum, a corresponding examination of the blood may also be performed already before the blood collection according to the invention. This is also recommendable because the blood can be discarded for the production of eye drops when contaminants are present.

Even if an analysis of the blood was performed before the collection, the new examination of the serum according to the invention represents additional safety in order to ensure improved product safety. According to the invention, it is possible to store the serum at a temperature of −20° C. before being filled into an administration means. In this case, the examination for contaminants is preferably effected after the storage and immediately before the filling into the administration means.

According to the invention, the serum is stored temporarily in a temperature-controlled refrigerator, especially until the results of the infection examination are available. If the infection tests show negative results, the corresponding batches can be filled into suitable administration means.

When the serum is filled in step d) of the process according to the invention, care should be taken that there is no contamination of the serum. Therefore, the filling in step d) is preferably performed in a cleanroom. This cleanroom may be in the vicinity of the place where the whole blood donation has been done. However, according to the invention, it is also possible that the serum or even the whole blood is at first shipped to a different place, and then the processing into the serum and/or the filling into administration means takes place in this, spatially separated, different place. It is to be taken care that a temperature of 10° C., especially 8° C., is not exceeded during the shipping.

Thus, according to the invention, another advantage over the method known from the prior art, as described, for example, in WO 2010/136535 A1, resides in the fact that the process according to the invention enables the site-independent production of eye drops prepared from the patient's own serum, which enables a more flexible application of the process according to the invention. If a large distance is to be covered by the final consumer for the blood collection and obtaining of the eye drops, this will often also lead to a lesser compliance by them. Now, with the process according to the invention, it is possible to perform a whole blood donation, for example, in the place of a transfusion physician. Even though the distance to be covered for this by the blood donator means some expenditure, this is still reasonable because of the low frequency of presumably twice a year. This also supports the compliance and thus the success of the treatment.

Therefore, using the process according to the invention, it is possible that the delivery of the eye drops prepared with their own serum to the patient can be done near their living place. If the place of blood collection is several kilometers remote from the patient's living place, then the load on the patient is merely to go there once in 6 months. After the separation of the blood, the process according to the invention enables the serum to be shipped, for example, to a pharmacy, which preferably has a cleanroom. In this pharmacy, the serum can then be filled into containers and delivered to the patient in single doses. Alternatively, it is also possible that the cleanroom is near the place where the blood collection takes place. In such a case, the shipping to a pharmacy near the living place can be effected after the filling into administration means. Thus, the process according to the invention enables an extremely high flexibility, which leads to eye drops prepared from the patient's own serum to be a supplied to them near their living place.

Therefore, the process preferably includes the following steps:
 a) collecting whole blood in a blood bag in a first place;
 b) separating the blood to obtain serum in said first place;
 b1) transferring said serum under sterile conditions into a serum bag in said first place;
 c) examining the serum for the presence of pathogens in said first place, then shipping the serum to a second place;
 d) filling the serum into at least one administration means in said second place.

Alternatively, and also preferably, the process includes the following steps:
 a) collecting whole blood in a blood bag in a first place, followed by shipping said whole blood to a second place;
 b) separating the blood to obtain serum in said second place;
 b1) transferring said serum under sterile conditions into a serum bag in said second place;
 c) examining the serum for the presence of pathogens in said second place; and
 d) filling the serum into at least one administration means in said second place.

Said filling of the serum into administration means can be simply effected, for example, by means of a three-way valve. The three-way valve is connected with a port to a bag in which the serum is contained (serum bag). Corresponding bags usually have a flexible tube, to which the three-way valve can be connected. The administration means can then be connected to another port of the three-way valve. The filling of the serum into the administration means is then controlled by the position of the valve. Depending on the volume of the serum and the volume of the administration means, it is possible to connect another serum bag to the third port of the three-way valve, in order to enable a complete filling of the administration means. However, this is not preferred, because cross-contaminations between the serum batches may occur in such a case. Preferably, another administration means is connected to the three-way valve. The process according to the invention enables a large volume of serum to be obtained. If it is not possible to fill the entire serum into one administration means, a new administration means would have to be connected to the serum bag. By using the three-way valve, this change can be avoided, and the whole volume of serum can be filled into appropriate administration means.

The filling is preferably performed in a cleanroom. This avoids further infection of the serum. Preferred administration means within the meaning of the present invention include administration containers.

Suitable administration containers are known from the prior art. A possible administration container, which is described in DE 20 2011 004 487 U1, includes a collection and ventilation container, which is connected with the administration containers through a final line, wherein said administration containers are each provided with opening means and are interconnected in a flowable manner. The administration containers can be connected to the serum bag through a sterile piece of flexible tube, for example, by means of a three-way valve. The individual administration containers each have a volume of about 3 ml.

A drawback resides in the fact that the flexible tube system, by which the administration containers are interconnected, has a volume in which serum accumulates that is not available for use as eye drops prepared from the patient's own serum (dead volume). In addition, the individual administration containers are made of a flexible or soft material. Different drop volumes are delivered, depending on the pressure applied. The volumes applied for the therapy and the duration of the therapy to be derived therefrom are not predictable. In addition, the large opening carries a high risk of contamination of the bottle content, for example, with bacteria or fungi. As soon as the single doses are opened, they cannot be closed again, so that the eye drops available in each administration container must be consumed within a few hours, or discarded because of the risk of contamination. Because of the high dead volume and the extremely short storage stability of the individual administration containers, the amount of eye drops available is low in comparison with the amount of collected blood, so that several blood collections are necessary to supply patients with a sufficient amount of eye drops over an extended period of time.

Preferably, the administration container is a pump system including a container for receiving the eye drops and a pumping device for metering the eye drops into the eye. The pump system has a design enabling it to be used several times. For example, the amount of eye drops contained therein is sufficient to enable a supply with eye drops over a period of a week or longer. Significantly longer application periods per container are not desirable because of the risk of contamination.

The amount of collected serum is sufficient to enable several pump systems to be filled. One pump system is then delivered to the patient, while the others are preferably stored with cooling in the second place, especially in the pharmacy. Then, when needed, the eye drops are delivered to the patient. Since the pharmacy, i.e., the second place, is as close as possible to the living place, the compliance is not reduced thereby. At the same time, however, the necessary professional storage of the eye drops over an extended period of time is ensured. During or before each delivery of eye drops in the pharmacy, it is verified whether the eye drops can still be employed, and the patient can be noticed in due time of the necessity of a new blood collection, so that a constant supply of eye drops and the control thereof is ensured without a large expenditure for the patient, i.e., the user of the eye drops, since the second place can be chosen near the living place or in another suitable place, such as close to the working place.

Particularly preferred are pump systems having such a design that microbial contamination of the eye drops during use is essentially avoided. This can be ensured by the design of the pumping device, in which, for example, a membrane can be contained through which the eye drops can get outside, but pathogens cannot get inside the pump system. Alternatively, the pumping device may also include an antibacterial device, such as a silver spiral. Corresponding pump systems are described, for example, in EP 1 380 351 A1.

Therefore, in a preferred embodiment, the process includes the following steps:
a) collecting whole blood in a blood bag in a first place, followed by shipping said whole blood to a second place;
b) separating the blood to obtain serum in said second place;
b1) transferring said serum under sterile conditions into a serum bag in said second place;
c) examining the serum for the presence of pathogens in said second place; and
d) filling the serum into at least one administration means in said second place, wherein said administration means is a pump system including a container for receiving the eye drops and a pumping device for metering the eye drops into the eye.

According to the invention, the filling of the serum is performed by withdrawing serum from the serum bag by means of a sterile syringe under sterile conditions, preferably in a cleanroom, and filling 5 ml each into the multidose dropping system (dosage bottle) with a pump system. The top pieces of the dosage bottles are mounted manually, a sleeve for protection of the bottles from being broken open is added, and tightly sealed onto the bottle by operating a lever press. The filter contained in the dosage bottle or in the pump system protects the serum from microbiological contamination. A silver spiral within the syringe prevents the growth of germs. Thus, the dead volume, i.e., the amount of serum that is discarded and not available as eye drops, is very low, whereby the number of blood collections can be kept low.

A corresponding pump system enables a defined individual dosage sequentially from the same container. As compared to other administration containers, there is an advantage here in that the eye drops obtained from the patient's own serum can be stored also over an extended period of at least 7 days in the patient's refrigerator, i.e., at a temperature of from +2° C. to +8° C., or even at room temperature, without there being contamination with aerobic or anaerobic bacteria or fungi. The contact of the eye drops with the silver spiral during the dosage thereof essentially keeps them free from microbes. At the same time, the efficiency of the eye drops is not affected.

Therefore, according to the invention, it is recommendable for the serum to be stored at a temperature $T \leq -20°$ C. after being filled into suitable administration containers. A storage of at least 6 months is possible without there being contamination of the eye drops. When the eye drops, having thus been stored in a deep frozen state, are thawed and stored at a temperature of from +2° C. to +8° C., or even at room temperature, they can be kept for at least 7 days or longer without contamination, and thus employed by the patient. Because of the process according to the invention, it is possible to supply the patient weekly with new eye drops close to their living place. Thus, it is ensured that the storage takes place at −20° C. in a pharmacy at a controlled temperature. Single doses, which can be kept in a household refrigerator, i.e., at a temperature of from +4° C. to +8° C., or at room temperature, for at least 7 days can then be delivered if needed. Thus, even those persons in which blood collection is not or only infrequently possible, for example, because of health problems, can be supplied with serum eye drops over a long period of time.

According to the invention, it is possible that the serum is diluted for preparing the eye drops, before or while being filled into suitable administration containers. Such dilution can be done, for example, by means of known artificial tear substitutes, which include, for example, isotonic saline and/or active ingredients, such as hyaluronic acid and/or lipids. The dilution may be within a range of from 10% to 30%. According to the present invention, this means that the eye drops consist of 90% by weight serum and 10% by weight tear substitute, based on 100% by weight of the eye drops. Accordingly, a dilution of 20% by weight means that the eye drops consist of 80% by weight serum and 20% by weight tear substitute, and a dilution of 30% by weight means that the eye drops consist of 70% by weight serum and 30% by weight tear substitute.

The dilution of the serum eye drops enables persons concerned to be supplied over a period of approximately one year, or even longer depending on the frequency of the application, which also results in an improved compliance. In addition, it has surprisingly been found that, when there are lesions of the cornea, such as those occurring in a leukemic disease, protein deposits may occur in the eye if undiluted serum eye drops are employed. Such protein deposits can be avoided by a dilution according to the invention.

Further, the dilution enables patients to be supplied over a long period, especially when they cannot go to the blood collection again because of some disease. This may be the case, for example, in a leukemic disease in which stem cells were transplanted for therapy. Patients concerned bear the risk that, because of an immune response against the transplanted stem cells, a "graft versus host disease", in which the cornea lesions in the eye as described above can occur in the patients, develops. These can also be treated well with serum eye drops. However, blood collection on a regular basis cannot be ensured because of the disease. The process according to the invention enables assistance here.

However, the dilution should not exceed a value of 30%. In a higher dilution, the flow properties of the eye drops will change, so that a good adhesion to the eye is no longer ensured. In addition, the further properties, such as the protein concentration, are also affected in such a way that the positive properties of the serum eye drops hardly outweigh conventional tear substitutes.

In addition to examining the serum for the presence of diseases and/or infections before the filling of the serum, it is further preferred according to the invention that also after the filling of the serum into administration containers, at least two administration containers are chosen on a random basis, and the serum contained therein is again examined for the presence of diseases and/or infections. Since a larger amount of blood is collected at the beginning according to the invention, a sufficient amount of serum is available to supply the patient with eye drops over a period of at least half a year on the one hand, and to ensure by a sufficient number of random samples that a further contamination has not occurred during the filling in step d) of the process according to the invention, on the other.

In another embodiment, the present invention further relates to eye drops prepared by the process according to the invention. The eye drops prepared by the process according to the invention ensure long-term supply close to the living place. Because only one blood donation is necessary, and because of an improved safety from infections based on the possibility to test the serum, an improved compliance and thus increased chances for a successful treatment of the dry eye syndrome result.

According to the invention, the eye drops can be used for treating the dry eye syndrome. Thus, for example, patients suffering from dry eyes in addition to the basic disease, such as diabetes or rheumatism, can employ corresponding eye drops. Further, the eye drops according to the invention are suitable for treating dry eyes occurring as side effects of drugs, such as hormone preparations, beta blockers, or psychopharmaceuticals. Lesions of the cornea, as may be caused by chemotherapeutic agents, may also be treated with the eye drops according to the invention. The eye drops are not only suitable for disease-related dry eyes, but may also be used by persons who are working very long with computer screens, or in particularly dry and cold rooms because of their working place.

Further, the present invention relates to a kit comprising the eye drops in a suitable administration container.

Suitable administration containers are known from the prior art, enabling the eye drops to be dosed at a constant rate. An administration container comprising a pump system having a container for receiving the eye drops and a pumping device for dosing the eye drops is preferred, because the amount of eye drops dosed during the use remains constant.

EXAMPLES

Example 1

Within the scope of a whole blood donation, 20 ml of blood was collected from each of 5 persons for examining the flow properties and the sterility of serum eye drops. The blood collection was performed by means of ACD-free blood collection tubes. The corresponding blood collection tubes have no coagulation inhibitors (ACD: acid-citrate-dextrose), so that the blood can be employed in the process according to the invention. After the blood collection, the coagulation was performed at room temperature in upright tubes. The coagulation was complete when the blood clot comprising the solid components of the blood could be detached from the vessel wall by a spatula. This could be done after 20 to 30 minutes.

After the blood clot had been removed from the tubes, the serum contained therein was centrifuged at 3500 revolutions/min for 20 min. Immediately thereafter, the serum supernatant was pipetted off, and the thus obtained serum was stored in a refrigerator at a temperature of from 4° C. to 8° C.

The serum was filled into administration containers with a pump system, as sold by the company Aero Pump GmbH as an eye dropper system with 3K® system. The following ready-to-use eye drops were obtained:

Example ED 1: 5 ml of serum in the administration container
Example ED 2: 5 ml of serum eye drops (10% dilution with isotonic saline)
Example ED 3: 5 ml of serum eye drops (20% dilution with isotonic saline)
Example ED 4: 5 ml of serum eye drops (30% dilution with isotonic saline)

A dilution of 10% means that 90% by weight of the serum eye drops is serum, and 10% by weight is isotonic saline. The same applies to the other dilutions, mutatis mutandis.

The storage of the ready-to-use eye drops was effected in a refrigerator at a temperature of from 4° C. to 8° C. Samples from the respective eye drops ED1 to ED4 were taken 5 times a day over a period of 9 days.

All the samples had a very good flowability and a slightly pink color, which decreased as the dilution increased. The samples taken constantly had the same volume. Even after 9 days, a microbial contamination of the eye drops could not be seen.

Example 2

Whole blood (500 ml) was collected from 10 persons according to standard methods of the DRK Blood Donation Service (standard operation procedure) into blood bags. After coagulation of the blood (over night at room temperature) and centrifugation (15 minutes at 3000 revolutions/min), the serum was transferred into empty bags thermally sealed to the blood bag.

The serum was transported into a cleanroom (class A in B) at +4° C. Therein, the serum was filled into administration containers with a pump system as sold by the company Aero Pump GmbH as an eye dropper system with 3K® system. The samples were stored each in a different way, and examined for sterility before being filled and thereafter.

Example ED5: Serum before being filled into the administration container
Example ED6: Serum in pump system after 48 h storage at −20° C.

Example ED7: Serum in pump system after 48 h storage at +4° C. to +8° C.

Example ED8: Serum in pump system after 48 h storage at room temperature (20° C.)

Example ED9: Serum in pump system after 5 days storage at room temperature (20° C.)

In all of Examples ED5 to ED9, the sterile controls performed (tests according to European Pharmacopoeia for aerobic and anaerobic germs and fungi) were negative. The controls were performed with an automated detection method BacT/Alert of Bio Merieux, Nürtingen, Germany.

The invention claimed is:

1. A process for producing ready-to-use eye drops, comprising the following steps:
    a) collecting at least 200 mL of whole blood in a first place, followed by
    b) separating the blood to obtain serum,
    c) examining the serum for the presence of pathogens, followed by
    d) filling the serum into at least one administration means in a second place,
    wherein said first and second places are different.

2. The process according to claim 1, further comprising: examining said serum for sterility before the eye drops are released as a medicament.

3. The process according to claim 1, characterized in that said whole blood is autologous or allogenic.

4. The process according to claim 1, characterized in that the filling in step d) is performed in a cleanroom.

5. The process according to claim 1, comprising the following steps:
    a) collecting whole blood in a blood bag in a first place, followed by shipping said whole blood to a second place;
    b) separating the blood to obtain serum in said second place;
    b1) transferring said serum under sterile conditions into a serum bag in said second place;
    c) examining the serum for the presence of pathogens in said second place; and
    d) filling the serum into at least one administration means in said second place, wherein said administration means is a pump system including a container for receiving the eye drops and a pumping device for metering the eye drops into the eye.

6. The process according to claim 1, characterized in that said serum is diluted before or while being filled in step d).

7. The process according to claim 6, characterized in that the dilution is within a range of from 10% to 30%.

8. The process according to claim 6, characterized in that the dilution is performed with known tear substitutes, especially with isotonic saline.

* * * * *

UNITED STATES PATENT AND TRADEMARK OFFICE
CERTIFICATE OF CORRECTION

PATENT NO. : 10,300,088 B2
APPLICATION NO. : 15/559653
DATED : May 28, 2019
INVENTOR(S) : Schrott et al.

Page 1 of 1

It is certified that error appears in the above-identified patent and that said Letters Patent is hereby corrected as shown below:

On the Title Page

Column 1 (30) Foreign Application Priority Data:
Change "Mar. 24, 2015 (DE) .......................... 10 2015 205 293"
To Mar. 24, 2015 (DE) .......................... 10 2015 205 293.1

Signed and Sealed this
Sixteenth Day of July, 2019

Andrei Iancu
*Director of the United States Patent and Trademark Office*